United States Patent [19]

Dugger

[11] Patent Number: 4,978,533
[45] Date of Patent: Dec. 18, 1990

[54] LIQUID NIFIDIPINE COMPOSITION

[75] Inventor: Harry A. Dugger, Flemington, N.J.

[73] Assignee: Pharmaconsult, Inc., Flemington, N.J.

[21] Appl. No.: 265,706

[22] Filed: Nov. 1, 1988

[51] Int. Cl.⁵ .................................................. A61K 9/66
[52] U.S. Cl. ...................................... 424/456; 424/455
[58] Field of Search ........................................... 424/456

[56] References Cited

U.S. PATENT DOCUMENTS 3,971,796  7/1976  Bossert et al. .......................... 514/929
4,430,333  2/1984  Campbell et al. ...................... 514/929
4,693,892  9/1987  Hegasy et al. ......................... 424/456

OTHER PUBLICATIONS

The Pharmacological Basis of Therapeutics, Goodman & Gilman, 7th edition, MacMillan Publishing Co., 1985, pp. 816-820.

*Primary Examiner*—Thurman K. Page
*Attorney, Agent, or Firm*—Wegner, Cantor, Mueller & Player

[57] ABSTRACT

A gelatin capsule form of nifedipine dosage unit containing from 12-20 parts by wt of glycerin per part by wt of nifedipine.

5 Claims, 4 Drawing Sheets

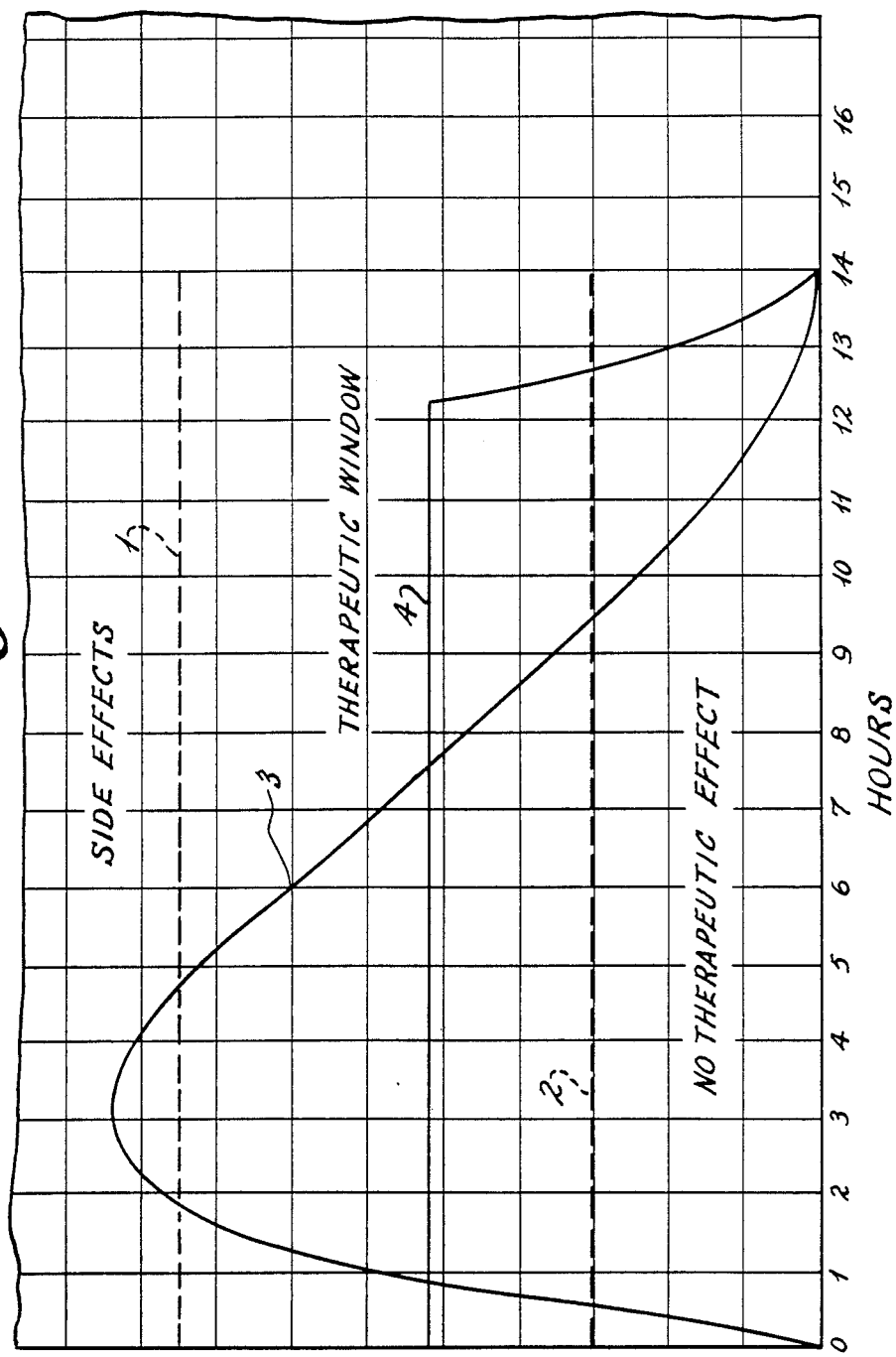

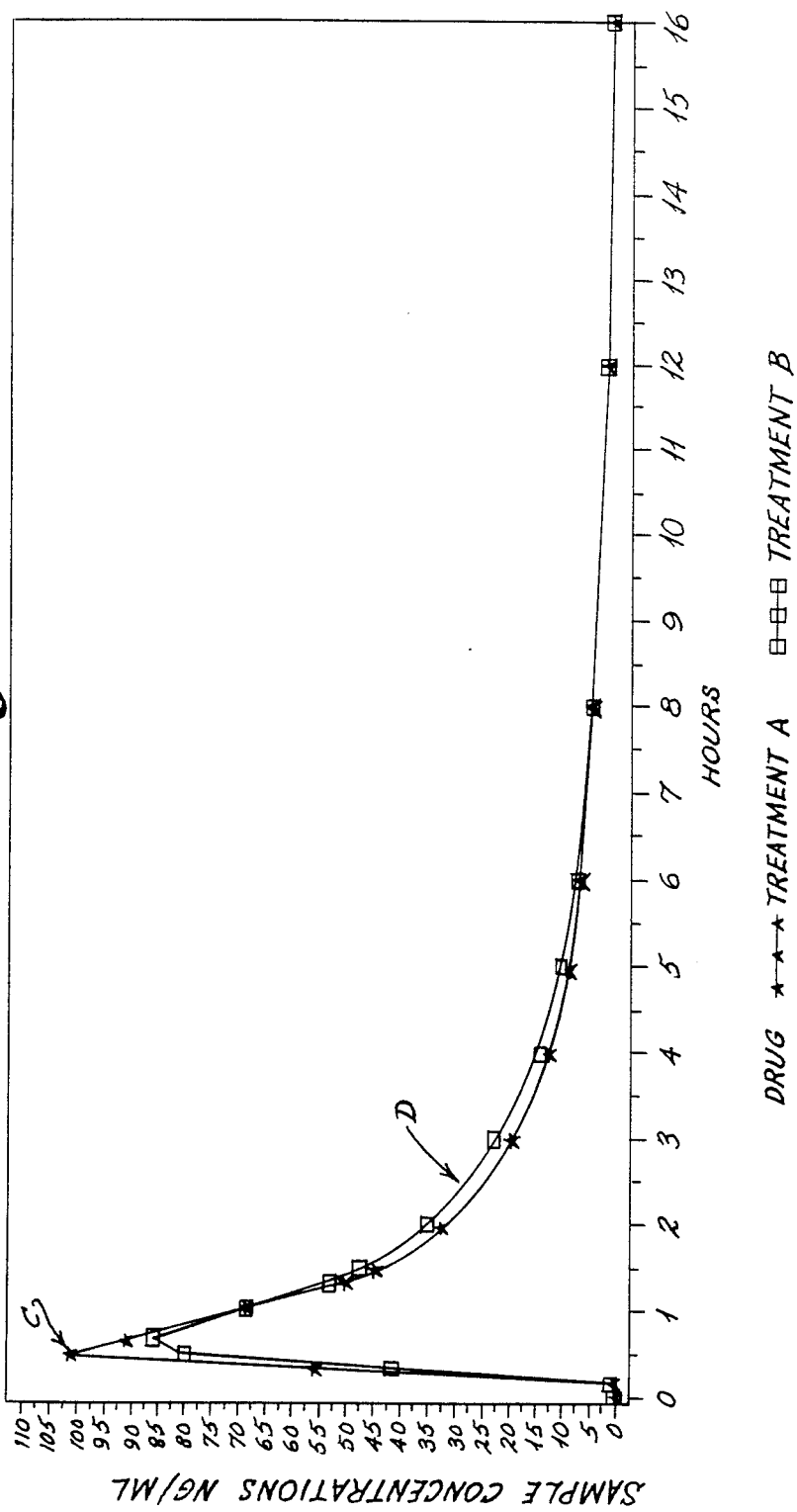

□ NIFEDIPINE, LEG II  + PROCARDIA, LEG I

□ NIFEDIPINE, LEG II  + PROCARDIA, LEG I

LIQUID NIFIDIPINE COMPOSITION

The present invention relates to a novel dosage unit for nifedipine, a widely used coronary dilator.

BACKGROUND

Nifedipine (which is characterized by effectiveness and rapid absorption from oral release capsules) is the generic name for the coronary dilator 4-(2'-nitrophenyl)-2,6-dimethyl-3,5-dicarbomethoxy-1,4-dihydropyridine and is a compound of the following formula:

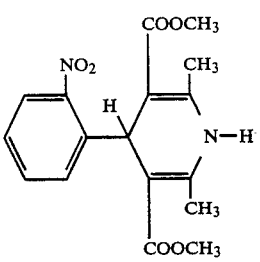

For discussion of oral release capsule dosage units of nifedipine and background to the improvement of this invention reference is made to U.S. Pat. No. 3,784,684 and to the earlier patents described therein.

RATIONALE OF THE INVENTION

Studies by the inventor hereof have ascertained that long accepted commercially available instant release capsule formulations (e.g., Procardia ™) may not, in fact, be an optimum formulations for many persons. Surprisingly, perhaps the nifedipine present in the capsule may be absorbed too rapidly.

It has been found that the proportion of solvent present in the (nifedipine containing) formulation significantly affects the absorption rate for the nifedipine. In some persons peak levels of the nifedipine in the blood will exceed the level required for adequate pharmacologic response, generating thereby possibility for adverse affects for an otherwise appropriate medicament dose in the instant release capsule.

THE INVENTION

Briefly stated, the present invention provides an instant release capsule nifedipine formulation containing from 12-20 parts by wt of glycerine per part by wt of nifedipine.

The capsule itself, the nifedipine dosage amount and the other ingredients present in the instant release formulation known in the art may be used as heretofore employed.

DISCUSSION OF THE INVENTION

For further understanding of the invention reference is made to the attached drawings wherein:

BRIEF DESCRIPTION OF THE DRAWINGS

FIG. 1 is a curve which graphically illustrates medicament level in the blood plotted against the time after administration relative to therapeutic window;

FIG. 2 is a curve comparing the median blood level responses of twenty-four subjects to a nifedipine formulation according to the present invention and a formulation according to the prior art (i.e., to Procardia ™).

Figure 3A:
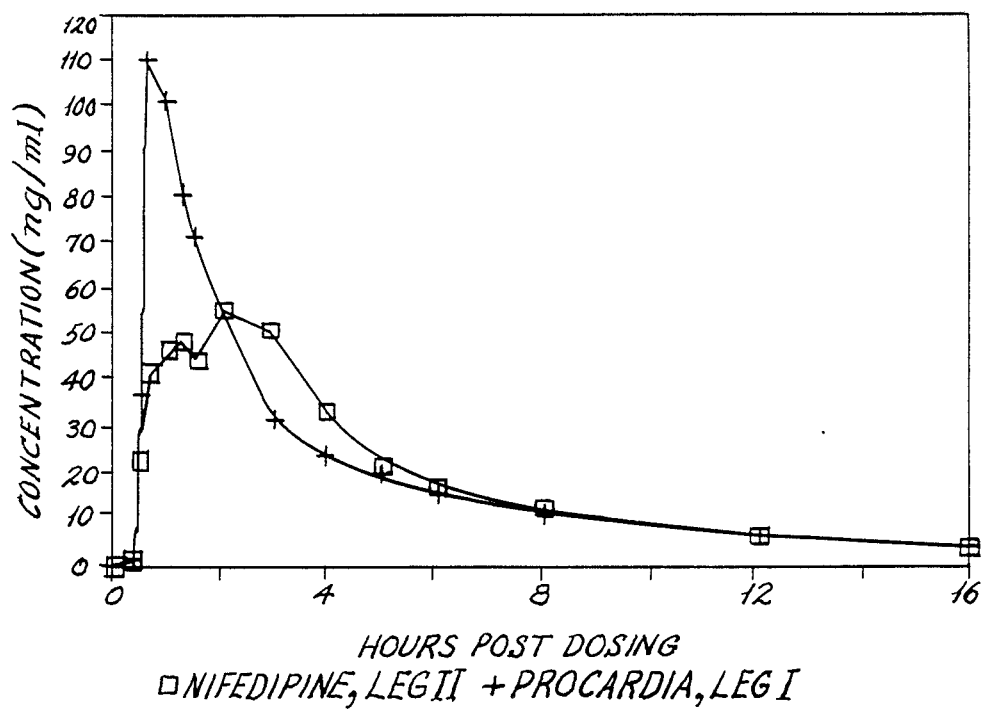
FIGS. 3A, B, C are curves showing the blood level response of three subjects to the nifedipine formulation according to practice of this invention and to Procardia ™.

Referring now to the generalized medicament response curve of FIG. 1, it may be seen thereon how the blood level concentration of any medicament varies over time. At the moment of administration no medicament is present in the subject's blood. Then, as the (administered) medicament is absorbed and becomes disseminated in the blood, the concentration of medicament in the blood rises to some peak level and thereafter, (absent further administration of the medicament) the concentration of medicament in the blood slowly declines as the medicament is metabolized or becomes excreted.

Typically, a therapeutic window exists, such being blood level concentrations within which the medicament generates the desired therapeutic effect. The window is between the concentration level at which the medicament fails to have the desired therapeutic effect, and some (higher) concentration at which undesired side effects generated by the medicament appear, or become unacceptably severe. Blood concentration levels that generate the therapeutic window are illustrated on FIG. 1 as horizontal lines 1, 2. FIG. 1 also illustrates blood concentration of the medicament against time curve 3, with curve 3 being drawn so that it generally resembles the blood concentration curve for nifedipine. In brief, the desired response to administration of nifedipine is rapid absorption, so that within 30 minutes after administration, the concentration of nifedipine in the blood has reached therapeutic levels, and thereafter for a relatively extended period of time relatively high concentrations of nifedipine remain in the blood so that, if continued medication with nifedipine is necessary, a repeat administration will not be needed for many hours, e.g., about 9 hours. It goes without more that the idealized square wave type of response, illustrated as curve 4, is not obtained with the prior art formulations, nor for that matter with the exemplary formulation of this invention.

It should be appreciated that FIG. 1 illustrates a generalized or theoretical representation of the concentration curve and therapeutic window for nifedipine. The actual concentration curve and therapeutic window for nifedipine will vary almost from patient to patient over a wide range and, accordingly, nifedipine instant release capsules are offered at several dosage levels. However, regardless of the particular dosage level employed, the response in each recipient subject will be curves similar to the general curves shown on FIG. 1 with, of course, higher peak blood concentration levels from administration of greater dosage capsules and lower peak levels from administration of lower dosage capsules. The dosage selected for each recipient is intended to generate blood concentration levels that fall within the therapeutic window of the recipient, yet not reach a level at which side effects become serious. Optimum dosage will vary from subject to subject and for some persons a relatively narrow therapeutic window will be found to exist. Side effects, e.g., dizziness, headache have been reported to occur in one of eight recipients of Procardia ™.

The area under the therapeutic response blood concentration curve 3 on FIG. 1 reflects total response to the dose administered. That portion of the nifedipine blood level concentrations in excess of the therapeutic window represents administration of what might be a harmfully excess level of nifedipine. Thus, in the generalized curve of FIG. 1, between hours 2 and 4 the subject exhibits excess nifedipine in the blood. Then over time blood level content declines until ultimately (after 9 hours) the blood level concentration of nifedipine falls below the therapeutic window, after which the nifedipine is without effect becoming wasted medicament, so to speak. Manifestly, the nifedipine would have the most beneficial effect if its administration generated the square wave of response of curve 4 (wherein medicament blood level increases very rapidly to a level within the therapeutic window, then remains essentially constant, and ultimately declines very rapidly).

FIG. 2 provides as curve D the mean response of 24 subjects to the exemplary nifedipine formulation of this invention hereinafter described, and as curve C their mean response to a known in the art nifedipine formulation (Procardia TM). It may be noticed that a modest, but significant reduction in peak blood level concentration $C_{max}$ is shown in Curve C to take place with practice of this invention.

As is very common in biological systems, subject to subject response (to administration of nifedipine) varied greatly. Some subjects actually generated slightly a higher $C_{max}$ level. Some subjects, however, generated the very favorable response curves illustrated as FIG. 3 A, B, C. Illustrated there are the blood level concentration curves obtained upon administration of equal dosage amounts of nifedipine to three individuals of a formulation according to the prior art and a formulation according to the present invention. Both formulations generated the desired rapid response to nifedipine with little, if any differences in time to generate blood level concentrations within the therapeutic window. For each subject the ($C_{max}$) peak concentration level attained from the exemplary formulation of this invention was considerably lower. Subjects 1 and 2 experienced a superior decline rate as well.

Figure 3B:
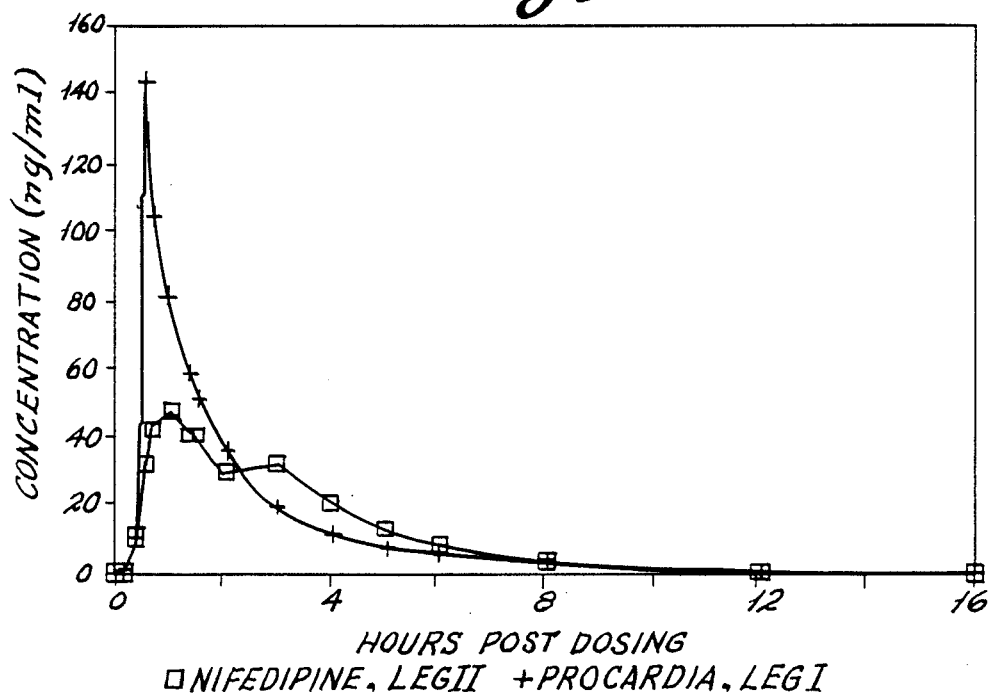
Figure 3C:
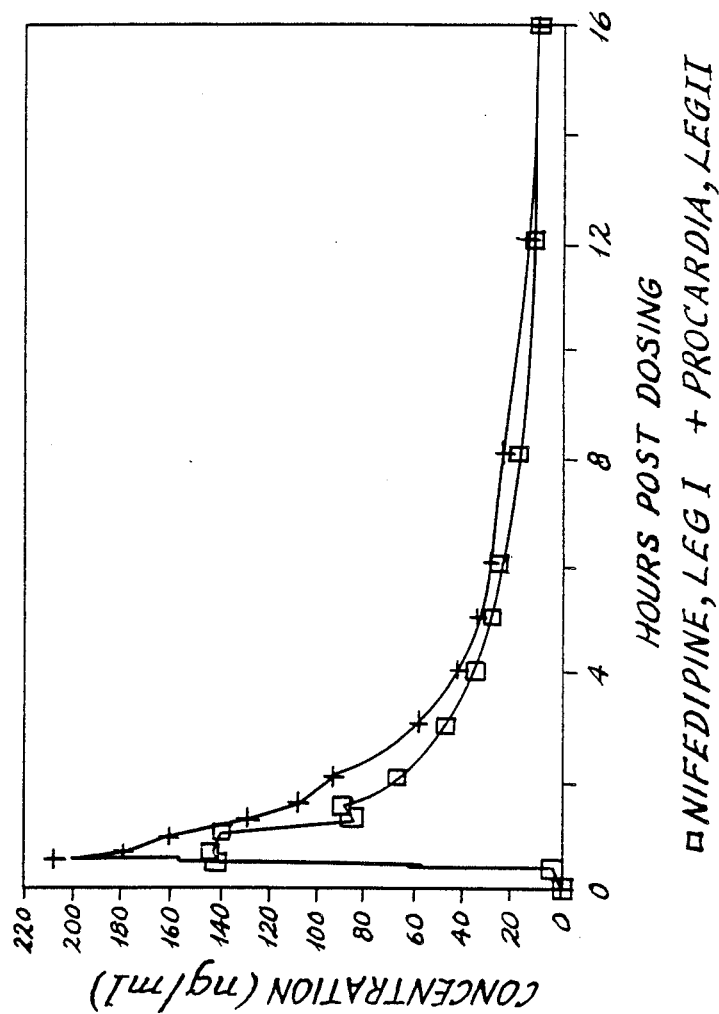

The differences in response time, namely, a perhaps slightly slower onset evidenced on FIG. 3 A, B, C is not believed to be material. The extended high concentration level shown in FIG. 3A, B is believed to be advantageous whenever such occurs, particularly when accompanied by the substantially reduced $C_{max}$ peak blood concentration levels. Administration of a nifedipine formulation according to practice of this invention is advantageous for those individuals wherein since the high peak response ($C_{max}$) individuals represents an excess therapeutic dose. Reducing the $C_{max}$ to the extent evidenced in FIG. 3 A, B, C will reduce the severity of undesired side effects arising from treatment with nifedipine and, hopefully, many individuals can avoid occurrence of undesired side effects by practice of this invention.

PRACTICE OF THE INVENTION

The reduced $C_{max}$ evidenced on FIGS. 2 and 3 A, B, C is obtained by employment of glycerin as the solvent in the nifedipine formulation capsule and by employing a glycerin to nifedipine (the active material) proportion which is in the range of 12:1 parts by wt to 20:1 parts by wt. The other components in the nifedipine formulation and the capsule itself, e.g., gelatin capsules, are as hitherto was prevalent in the art. Thus, for example, the formulations suggested in the already referenced U.S. Pat. No. 3,784,684 may be employed save only for the presence of glycerin in the above described proportions and appropriately a reduction in amount of polyethylene glycol. A preferred formulation for nifedipine capsules USP 10 mg is as follows.

| Nifedipine Capsules USP 10 mg | |
|---|---|
| Composition | |
| Capsule Fill: | |
| Active Ingredients: | |
| Nifedipine | 10.15 mg |
| Inactive Ingredients: | |
| Polyethylene Glycol 400 | 490.00 mg |
| Glycerin 98% | 150.00 mg |
| Menthol | 0.87 mg |
| Total Capsule Fill: | 651.02 mg |
| Capsule Shell: | |
| Inactive Ingredients: | |
| Gelatin | 174.44 mg |
| Glycerin 98% | 48.57 mg |
| Anidrisorb 85/70 | 29.31 mg |
| Purified Water | 175.00 mg |
| Ferric Oxide Red | 2.68 mg |
| Total Capsule Shell: | 430.00 mg |

For higher dosage capsules, e.g., 20 or 30 mg of nifedipine, only the fill ingredients of glycerin and nifedipine need be changed in amount, i.e., nifedipine will become 20 or 30 mg and glycerin is increased in proportion. To maintain capsule shell size the same polyethylene glycol content is reduced appropriately.

The curves on FIG. 2 and FIG. 3 A, B, C were obtained from administration of the 10 mg nifedipine dose formulation capsules made according to the foregoing exemplary composition. The curves representing prior art results were obtained by administration of 10 mg dose levels of procardia TM.

FURTHER DISCUSSION

The $C_{max}$ is believed to depend upon the rate at which nifedipine is absorbed by the subject's body after oral administration thereof and this in turn depends upon the availability of the nifedipine in the formulation for absorption. The glycerine/nifedipine ratio seems to affect absorption rate, i.e., varies the availability of nifedipine for absorption by the body. Manifestly a high level of immediate availability is desired with, however, some sort of limitation on absorption rate being desirable in order to reduce the $C_{max}$ level. A substantial glycerin content in the formulation appears to serve both purposes. Acceptably high dissolution rates are attained within the glycerin to nifedipine ratio (wt/wt) range of about 12:1 to 20:1. A ratio of about 15:1 of glycerin to nifedipine (wt/wt) is believed to be an optimum ratio.

The following laboratory test demonstrates that the dissolution rate of glycerin-nifedipine mixtures in (simulated) gastric juices is some function of the glycerin content.

Solutions of nifedipine were using Polyethylene glycol 400, nifedipine and varying proportions of glycerin were placed in the gelatin capsules. The ratio of glycerin to nifedipine was varied from 12:1 to 30:1. A series of 30 minute dissolution tests were carried out on the capsules filled with these mixtures in HCL solutions that simulated gastric fluid (using a paddle speed of 50 rpm); the results are shown in the following Table.

|   | Dissolution of Nifedipine (%) at 30 minutes |
| --- | --- |
| A. Glycerin/Nifedipine Ratio | |
| 12:1 | 88.4 |
| 15:1 | 90.0 |
| 20:1 | 82.1 |
| 30:1 | 71.8 |
| B. Procardia TM | 100.2 |

The results from this dissolution rate study is believed to be consistent with the test results graphed on FIGS. 2 and 3 A, B, C from formulations according to this invention. The about 90% dissolution rate indicated by the rate study generates a response comparable to the response rate found with prior art nifedipine formulations (e.g., with Procardia TM). Thus, soon after oral administration of the encapsulated nifedipine formulations sufficient nifedipine enters the blood stream to achieve the desired rapid therapeutic response. In addition, the modestly reduced dissolution rate vis Procardia TM of about 90% as against 100% indicated by the dissolution rate study explains the lower $C_{max}$ shown at FIG. 2 and for some subjects an attainment of a (desirable) more extended duration of high blood level concentrations of nifedipine (see the curves of FIGS. 3A, B).

I claim:

1. In a method of treating coronary insufficiency with nifedipine which comprises administering an orally ingestible therapeutic dosage amount of said nifedipine contained as a fill in a gelatin capsule shell, the improvement comprising including in said capsule fill about 12-20 parts by weight of glycerin per part by weight of said nifedipine.

2. The method of claim 1 wherein said capsule fill further comprises, a small but effective amount of flavoring agent, and a polyalkylene glycol.

3. In a rapid release medication for treating coronary insufficiency which comprises an orally ingestible gelatin capsule having therein a fill comprising a therapeutic dosage unit amount of nifedipine, the improvement comprising from 12-20 parts by weight of glycerin in said fill per part by weight of said nifedipine.

4. A rapid release medication according to claim 3, wherein said glycerin is present in said capsule fill in an amount of about 15 parts by weight per part of nifedipine.

5. A rapid release medication according to claim 3, further comprising a small but effective amount of a flavoring agent, and a sufficient amount of a polyalkylene glycol to fill said capsule.

* * * * *